(12) United States Patent
Wu et al.

(10) Patent No.: US 7,396,835 B2
(45) Date of Patent: Jul. 8, 2008

(54) PROCESS FOR THE PREPARATION OF TUBULIN INHIBITORS

(75) Inventors: Yanzhong Wu, Bronx, NY (US); Jean Schmid, Chester, NY (US); Jay Thomas Afragola, Spring Valley, NY (US); David Blum, Saddle River, NJ (US); Semiramis Ayral-Kaloustian, Tarrytown, NY (US)

(73) Assignee: Wyeth, Madison, NJ (US)

( * ) Notice: Subject to any disclaimer, the term of this patent is extended or adjusted under 35 U.S.C. 154(b) by 462 days.

(21) Appl. No.: 11/007,839

(22) Filed: Dec. 8, 2004

(65) Prior Publication Data

US 2005/0124635 A1 Jun. 9, 2005

Related U.S. Application Data

(60) Provisional application No. 60/527,931, filed on Dec. 8, 2003.

(51) Int. Cl.
*A01N 43/90* (2006.01)
*A61K 31/519* (2006.01)
*C07D 487/00* (2006.01)

(52) U.S. Cl. .................. 514/259.31; 544/263

(58) Field of Classification Search .............. None
See application file for complete search history.

(56) References Cited

U.S. PATENT DOCUMENTS

| | | | |
|---|---|---|---|
| 5,593,996 | A | 1/1997 | Pees et al. |
| 5,612,345 | A | 3/1997 | Becher et al. |
| 5,750,766 | A | 5/1998 | Krummel et al. |
| 5,756,509 | A | 5/1998 | Pees |
| 5,808,066 | A | 9/1998 | Krummel et al. |
| 5,817,663 | A | 10/1998 | Pees et al. |
| 5,854,252 | A | 12/1998 | Pees et al. |
| 5,948,783 | A | 9/1999 | Pees et al. |
| 5,955,252 | A | 9/1999 | Goto et al. |
| 5,965,561 | A | 10/1999 | Pees et al. |
| 5,981,534 | A | 11/1999 | Pfrengle |
| 5,985,883 | A | 11/1999 | Pees |
| 5,986,153 | A | 11/1999 | Kallenbach et al. |
| 5,994,360 | A | 11/1999 | Pfrengle |
| 6,020,338 | A | 2/2000 | Pfrengle et al. |
| 6,117,876 | A | 9/2000 | Pees et al. |
| 6,242,451 | B1 | 6/2001 | Pees |
| 6,297,251 | B1 | 10/2001 | Pees et al. |
| 2005/0090508 | A1* | 4/2005 | Zhang et al. ........... 514/259.31 |

FOREIGN PATENT DOCUMENTS

| | | | |
|---|---|---|---|
| EP | 0 562 615 | A1 | 9/1993 |
| EP | 0 770 615 | A1 | 5/1997 |
| EP | 0 782 997 | A2 | 7/1997 |
| EP | 0 550 113 | B1 | 10/1997 |
| EP | 0 834 513 | A2 | 4/1998 |
| EP | 0 562 615 | B1 | 6/1998 |
| EP | 0 945 453 | A1 | 9/1999 |
| EP | 0 989 130 | A1 | 3/2000 |
| EP | 0 770 615 | B1 | 6/2003 |
| FR | 2 784 381 | | 9/1999 |
| WO | WO 94/20501 | A1 | 9/1994 |
| WO | WO 98/41496 | A1 | 9/1998 |
| WO | WO 98/46607 | A1 | 10/1998 |
| WO | WO 98/46608 | A1 | 10/1998 |
| WO | WO 98/41255 | A1 | 8/1999 |
| WO | WO 99/48893 | A1 | 9/1999 |
| WO | WO 02/02563 | A2 | 1/2002 |

OTHER PUBLICATIONS

U.S. Appl. No. 11/451078, filed Jun. 2006, Wu et. al.*
Conley et. al.; 2001; Encyclopedia of Reagents for Organic Synthesis; Tripropylamine; p.1-3.*
Sorgi et. al.; Encyclopedia of Reagents for Organic Synthesis; Triethylamine; p. 1-12.*
Sorgi et. al.; 2001; Encyclopedia Reagents for Organic Synthesis; Diisopropylethylamine; p. 1-10.*
Gawley et. al.; 2006; Encyclopedia of Reagents for Organic Synthesis; Sodium Hydride; p. 1-20.*
Caine et. al.; 2006; Encyclopedia of Reagents for Organic Synthesis; Potassium t-Butoxide; p. 1-36.*
Rowinsky, E.K. and Tolcher, A.W.; Cancer Principles and Practice; Ed. 6; pp. 431-452; 2001.
Gottesman, M.M.; Annu. Rev. Med.; vol. 53; pp. 615-627; 2002.

* cited by examiner

*Primary Examiner*—James O. Wilson
*Assistant Examiner*—Jeffrey H Muarray
(74) *Attorney, Agent, or Firm*—Daniel B. Moran

(57) ABSTRACT

The present invention provides a process for the preparation of 6-[(substituted)phenyl]-triazolopyrimidine dicarboxylic acid salt and as a hydrated salt having the structural formula (I)

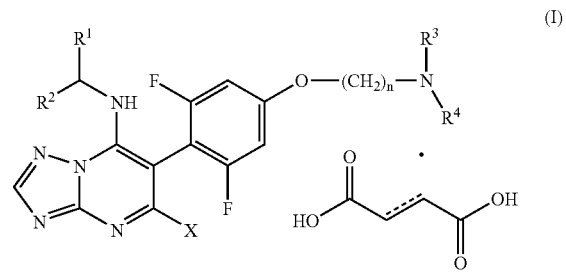

wherein:
$R^1$ is $CF_3$ or $C_2F_5$;
$R^2$ is H or $C_1$-$C_3$ alkyl;
n is an integer of 2, 3, or 4;
X is Cl or Br;
$R^3$ and $R^4$ are each independently H or $C_1$-$C_3$ alkyl; or
$R^3$ and $R^4$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^5$;
$R^5$ is $C_1$-$C_3$ alkyl;
wherein the dotted line is an optional bond.

29 Claims, No Drawings

PROCESS FOR THE PREPARATION OF TUBULIN INHIBITORS

This application claims priority from provisional application No. 60/527,931, filed Dec. 8, 2003, the entire disclosure of which is hereby incorporated by reference.

FIELD OF THE INVENTION

The present invention relates to a process for the preparation of triazolopyrimidine dicarboxylic acid salts which are tubulin inhibitors useful in the treatment of cancer.

BACKGROUND OF THE INVENTION

There is still a need in the art for cytotoxic agents for use in cancer therapy. In particular, there is a need for cytotoxic agents which inhibit or treat the growth of tumors which have an effect similar to paclitaxel and interfere with the process of microtubule formation. Additionally, there is a need in the art for agents which accelerate tubulin polymerization and stabilize the assembled microtubules.

Antimicrotubule drugs are a major category of anticancer agents (Rowinsky, E. K., and Tolcher, A. W. Antimicrotubule agents. In: V. T. Devita, Jr., S. Hellman, and S. A. Rosenberg (eds.), Cancer Principles and Practice, Ed. 6, pp. 431-452. Philadelphia: Lippincott Williams and Wilkins, 2001). Antimicrotubule drugs work by interfering with the function of cellular microtubules, particularly the mitotic spindle. The disruption of normal spindle function leads to apoptotic cell death.

Many tumors are inherently resistant (e.g., colon tumors) or become resistant after multiple cycles of treatment, at least in part due to the expression of drug transporters located in cancer cell membranes that pump the drugs out of cells and thereby decrease their efficacy (Gottesman, M. M. Mechanisms of cancer drug resistance. Annu. Rev. Med., 53: 615-627, 2002). The best known of these transporters is P-glycoprotein. Accordingly, there is a need for new agents with taxane-like effects on microtubule polymerization that are not substrates of P-glycoprotein or other such pumps and that therefore will overcome this cause of taxane resistance in patients.

It is an advantage to provide new compounds which provide a method of treating or inhibiting cell proliferation, neoplastic growth and malignant tumor growth in mammals by administering compounds which have paclitaxel like anticancer activity. It is an additional advantage to provide new compounds which provide a method for treating or inhibiting growth of cancerous tumors that express multiple drug resistance (MDR) or are resistant because of MDR. It is an additional advantage to provide new compounds which provide a method of treating or inhibiting the growth of cancerous tumors in a mammal with inherent or acquired resistance to chemotherapeutic agents and in particular antimitotic agents.

Accordingly, while there is ongoing research for new clinical candidates there is also a search for new and improved methods of preparation of those selected clinical candidates.

Described in WO 02/02563 A2 is the use of triazolopyrimidines having the structural formula

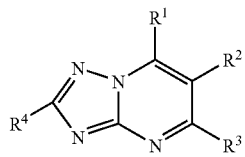

in cancer therapy, and in particular as microtubule agents. Previously described in U.S. Pat. Nos.: 5,593,996; 5,756,509; 5,948,783; 5,981,534; 5,612,345; 5,994,360; 6,020,338; 5,985,883; 5,854,252; 5,808,066; 5,817,663; 5,955,252; 5,965,561; 5,986,153; 5,750,766; 6,117,876; 6,297,251 and International Publication Numbers: WO98/46607; WO98/46608; WO99/48893; WO99/41255; EPO 834513A2; EPO 782997A2; EPO550113B1; FR2784381A1; EPO 989130A1; WO98/41496; WO94/20501; EPO 945453A1; EPO 562615A1; EP 077065 and EPO 562615B1 are the methods of preparation and the use of the above triazolopyrimidines in agriculture as fungicides.

Described in copending application No. 60/505,544, filed Sep. 24, 2003 is a series of 6-[(substituted)phenyl]-triazolopyrimidine compounds having the structural formula

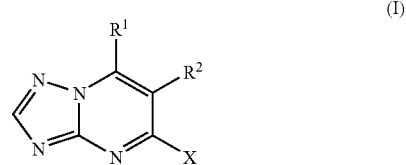

(I)

which are microtubule inhibitors and useful in the treatment of cancer.

Often, a process which works in the laboratory is not practical for large-scale preparations. In particular, the reported synthesis of 5,7-dichloro-6-(substituted-phenyl)-[1,2,4]triazolo[1,5-a]pyrimidine prepared by cyclization of 2-(substituted-phenyl)-malonic acid diethyl ester with 1-amino-2,3,5-triazole is described in U.S. Pat. No. 6,117,876 and further described in EP 0 770 615 A1 and EP 0 770 615 B1 where 6-(substituted-phenyl)-[1,2,4]triazolo[1,5-a]pyrimidine-5,7-diol is formed and chlorinated by reaction with phosphorus oxychloride to give 5,7-dichloro-6-(substituted-phenyl)-[1,2,4]triazolo[1,5-a]pyrimidine. While the described series of steps may be completed on a small scale in a single vessel, the addition of chlorinating reagent, phosphorous oxychloride at 130° C. following removal of ethanol by distillation, is difficult to perform in large-scale preparations. Further the above described process is limited to small-scale synthesis because the resulting product as an oil is difficult to purify.

U.S. Pat. No. 5,986,135 and U.S. Pat. No. 6,117,876 describe a method for the preparation of [5-chloro-6-(substituted-phenyl)-[1,2,4]triazolo[1,5-a]pyrimidin-7-yl]-((1S)-2,2,2-trifluoro-1-methyl-ethyl)-amine, through amination of 5,7-dichloro-6-(substituted-phenyl)-[1,2,4]triazolo[1,5-a]pyrimidine with (S)-2,2,2-trifluoro-1-methyl-ethylamine.

The method however is not entirely satisfactory because an oily intermediate, which lacks a practical method of purification, is formed when preparing the 5,7-dichloro-6-(substituted-phenyl)-[1,2,4]triazolo[1,5-a]pyrimidine and further the subsequent reaction with (S)-2,2,2-trifluoro-1-methylethylamine is performed.

Clearly there is need to provide a new process for the preparation of 6-[(substituted)phenyl]-triazolopyrimidine compounds which overcomes the drawbacks of the prior art processes. In particular, there is a need for a process to prepare purified crystalline 6-[(substituted)phenyl]-triazolopyrimidine compounds.

Further there is a need to provide a new process which in comparison with those described in the above mentioned art represents a significant advance over the art.

In light of the usefulness of the triazolopyrimidine compounds in cancer therapy, there is a need to develop simpler and milder methods for their preparation.

SUMMARY OF THE INVENTION

The present invention provides a process for the preparation of a 6-[(substituted)phenyl]-triazolopyrimidine dicarboxylic acid salt and as a hydrated salt having the structural formula (I)

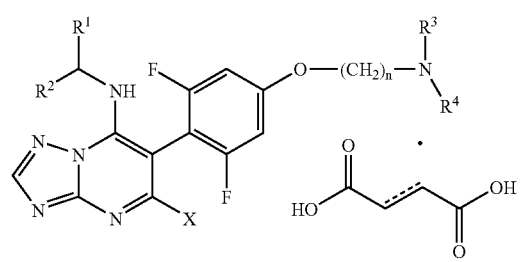

wherein:
$R^1$ is $CF_3$ or $C_2F_5$;
$R^2$ is H or $C_1$-$C_3$ alkyl;
n is an integer of 2, 3, or 4;
X is Cl or Br;
$R^3$ and $R^4$ are each independently H or $C_1$-$C_3$ alkyl; or
$R^3$ and $R^4$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^5$;
$R^5$ is $C_1$-$C_3$ alkyl;
wherein the dotted line is an optional bond, which process comprises:
a. reacting a malonic acid ester of the formula

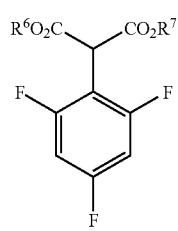

where $R^6$ and $R^7$ are independently $C_1$-$C_3$ alkyl with 3-amino-1,2,4-triazole, in the presence of trialkylamine base and heating at about 130-170° C., for about 1 to 6 h, cooling to about 130° C., diluting with toluene, cooling from about 20° C. to about 30° C., and adding at least two equivalents of aqueous alkali metal hydroxide (MOH) and isolating the dimetal salt of the formula

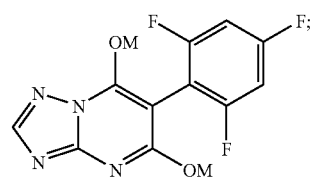

b. halogenating the dimetal salt with a halogenating reagent $POX_3$ where X is Br or Cl to obtain the halogenated product of the formula

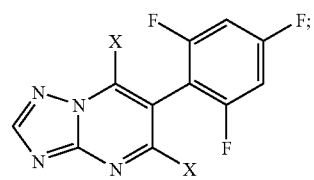

c. reacting the halogenated product with an amine

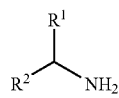

in an aprotic solvent from about 20° C. to about 30° C. to obtain the amine product of the formula

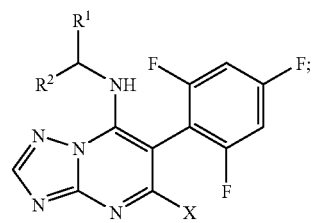

d. reacting an alkali metal hydride with an aminoalcohol HO—$(CH_2)_n$—$NR^3R^4$ for about 30 minutes in tetrahydrofuran at about 10 to 40° C., adding the amine product and heating to about 55-60° C. for about 12 to 20 h, to obtain the 6-[(substituted)phenyl]-triazolopyrimidine product

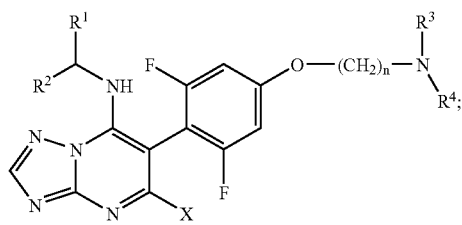

e. reacting the 6-[(substituted)phenyl]-triazolopyrimidine product in water with a dicarboxylic acid of the formula

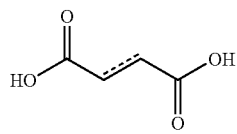

wherein the dashed line is an optional bond and adding a solvent selected from t-butylmethyl ether, ethyl acetate and toluene, to obtain the 6-[(substituted)phenyl]-triazolopyrimidine dicarboxylic acid salt as a solid

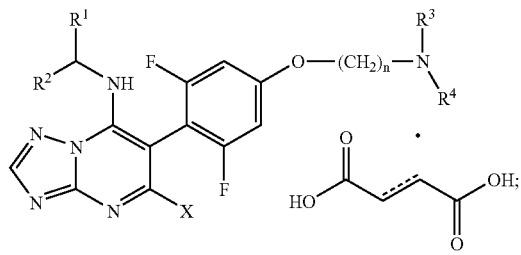

f. crystallizing the 6-[(substituted)phenyl]-triazolopyrimidine dicarboxylic acid salt from water and collecting the 6-[(substituted)phenyl]-triazolopyrimidine dicarboxylic acid salt;

g. forming the anhydrous 6-[(substituted)phenyl]-triazolopyrimidine dicarboxylic acid salt by drying the 6-[(substituted)phenyl]-triazolopyrimidine dicarboxylic acid salt; and h. treating the anhydrous 6-[(substituted)phenyl]-triazolopyrimidine dicarboxylic acid salt with water to obtain a 6-[(substituted)phenyl]-triazolopyrimidine dicarboxylic acid salt of formula (I) as a hydrated salt

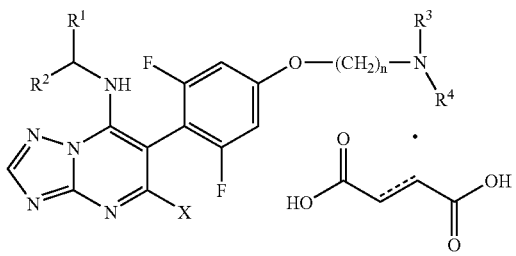

(I)

Especially preferred is a process for preparing a 6-[(substituted)phenyl]-triazolopyrimidine dicarboxylic acid salt and as a hydrated salt of formula (II)

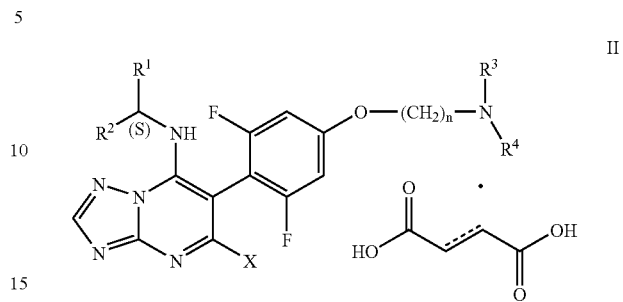

II wherein:
$R^1$ is $CF_3$ or $C_2F_5$;
$R^2$ is H or $C_1$-$C_3$ alkyl;
n is an integer of 2, 3, or 4;
X is Cl;
$R^3$ and $R^4$ are each independently H or $C_1$-$C_3$ alkyl;
wherein the dotted line is an optional bond,
which process comprises
a. reacting a malonic acid ester of the formula

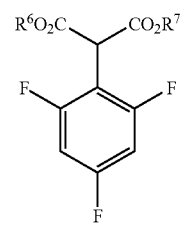

where $R^6$ and $R^7$ are independently $C_1$-$C_3$ alkyl with 3-amino-1,2,4-triazole, in a mole ratio of about 1:1 in the presence of tributylamine and heating at about 130-170° C. for about 1-6 h, cooling to about 130° C., diluting with toluene, cooling to about 20-30° C., and adding at least two equivalents of aqueous sodium hydroxide and isolating the disodium salt of the formula

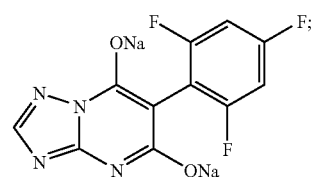

b. halogenating the disodium salt with a halogenating reagent $POX_3$ where X is Cl by heating to reflux for about 16 h to obtain the halogenated product of the formula

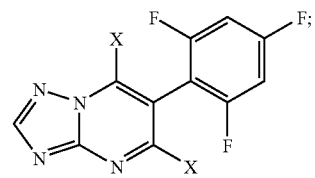

c. reacting the halogenated product with an amine

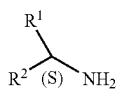

in an aprotic solvent from about 20° C. to about 30° C. for about 18-24 hours to obtain an amine product of the formula

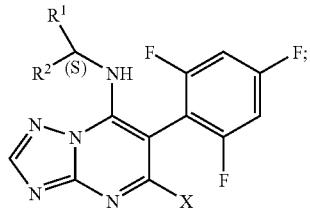

d. reacting an alkali metal hydride with an aminoalcohol HO—(CH$^2$)$_n$—NR$^3$R$^4$ for about 30 minutes in tetrahydrofuran at about 20-30° C., adding the amine product and heating to about 55-60° C. for about 14-16 hours to obtain the 6-[(substituted)phenyl]-triazolopyrimidine product

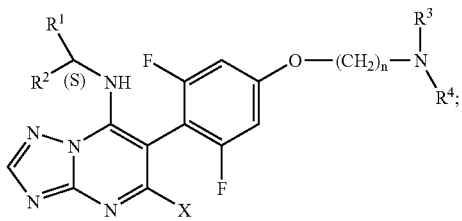

e. reacting the 6-[(substituted)phenyl]-triazolopyrimidine product in water with a dicarboxylic acid of the formula

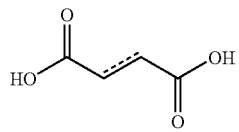

wherein the dashed line is an optional bond and adding t-butylmethyl ether to obtain the 6-[(substituted)phenyl]-triazolopyrimidine dicarboxylic acid salt as a solid

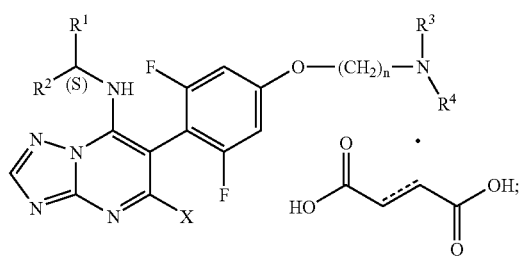

f. crystallizing the 6-[(substituted)phenyl]-triazolopyrimidine dicarboxylic acid salt from water and collecting the 6-[(substituted)phenyl]-triazolopyrimidine dicarboxylic acid salt;

g. forming the anhydrous 6-[(substituted)phenyl]-triazolopyrimidine dicarboxylic acid salt by drying the 6-[(substituted)phenyl]-triazolopyrimidine dicarboxylic acid salt; and h. treating the anhydrous 6-[(substituted)phenyl]-triazolopyrimidine dicarboxylic acid salt with water in a saturated water atmosphere to obtain a 6-[(substituted)phenyl]-triazolopyrimidine dicarboxylic acid salt as a hydrated salt of formula (II)

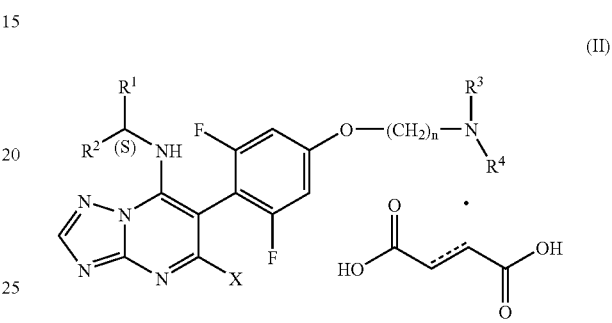

A particular embodiment of the invention comprises an effective and efficient process for the preparation and purification of the succinate salt of [5-chloro-6-(2,4,6-trifluoro-phenyl)-[1,2,4]triazolo[1,5-a]pyrimidin-7-yl]-((1S)-2,2,2-trifluoro-1-methyl-ethyl)-amine of formula (A) and especially as the dihydrated form (B).

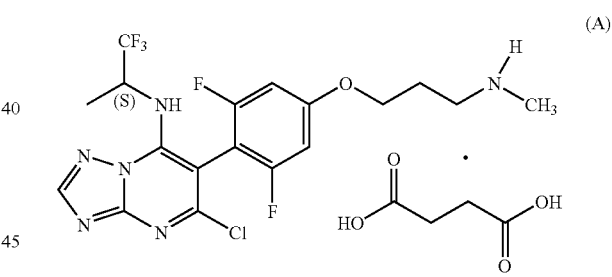

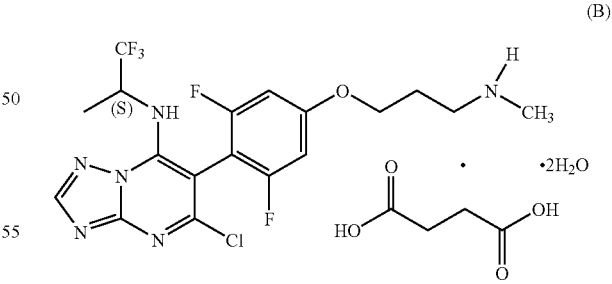

In a further more preferred embodiment, R$^3$ and R$^4$ are each independently H or C$_1$-C$_3$ alkyl.

In an additionally preferred embodiment, R$^3$ is H and R$^4$ is methyl.

The compounds prepared by the process of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. Included in the scope of the present invention are (R) and (S) isomers of compounds of general formula (I) having a chiral center and the racemates thereof. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Definitions

The term alkyl means a straight or branched alkyl of 1 to 4 carbon atoms, preferably 1 to 3 carbon atoms.

Halogenating agent, means a brominating or chlorinating agent $POX_3$ wherein X is Br or Cl, preferably phosphorus oxybromide or phosphorus oxychloride.

Aprotic solvent includes as a solvent N,N-dimethylformamide.

Alkali metal hydride includes lithium, potassium or sodium hydride.

The term alkali metal hydroxide includes potassium or sodium hydroxide, preferably about 50% aqueous sodium hydroxide.

Trialkylamine base includes tributylamine and tripropylamine.

Dicarboxylic acid means an acid of the formula

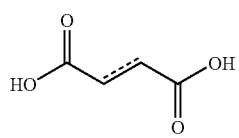

where the dotted line is an optional bond. Exemplary dicarboxylic acids include succinic acid and fumaric acid.

The term hydrated salt means a dicarboxylic acid salt of Formula (I) or (II) with bound water, wherein up to five moles or a fraction of whole moles (ie 2.5 moles) may be bound, preferably two moles of water as the dihydrate.

DETAILED DESCRIPTION OF THE INVENTION

In the new process for the preparation of 6-[(trisubstituted)phenyl]triazolopyrimidine compounds as described in Scheme 1, 2-(2,4,6-trifluoro-phenyl)-malonic acid diester 1 is reacted with 3-amino-1,2,4-triazole in a mole ratio of about 1:1 in the presence of a trialkylamine base, preferably tributylamine at a temperature range of about 130° to about 170° C., preferably at about 150° C. for a time of about 1 to 6 h, preferably in the range of about 2 to about 3 h. The reaction mixture on cooling to about 130° C. is taken into toluene and treated with at least 2 equivalents of alkali metal hydroxide, preferably sodium hydroxide as a solution and more preferred as a solution of about 50% aqueous sodium hydroxide, in a temperature range of about 10° C. to 50° C. and stirring for about 1 to 3 h preferably from about 20° C. to about 30° C., more preferred about 25° C., forming a solid. The resulting solid is filtered, washed with toluene and dried at about 80° C. under vacuum to give disodium salt of 6-(2,4,6-trifluorophenyl)-[1,2,4]triazolo[1,5-a]pyrimidine-5.7-diol 2, in quantitative yield with a purity of >95% by high pressure liquid chromatography (HPLC).

In the second step of the above process, to the isolated disodium salt of 6-(2,4,6-trifluorophenyl)-[1,2,4]triazolo[1,5-a]pyrimidine-5.7-diol 2 over a time of about 20 to about 60 minutes preferably about 30 minutes is added a halogenating agent, preferably a brominating or chlorinating agent $POX_3$ wherein X is Br or Cl, more preferred phosphorus oxybromide or phosphorus oxychloride in a ratio of 2-8 mL/g of disodium salt of 6-(2,4,6-trifluorophenyl)-[1,2,4]triazolo[1,5-a]pyrimidine-5.7-diol and heated to reflux for about 8 to about 24 h, preferably about 16 h. The volatiles are removed by distillation to a residue which is distilled with toluene at least two times to afford a residue. The residue is dissolved in a solvent selected from ethyl acetate, dichloromethane or toluene and poured into water while maintaining the temperature between about 5-15° C. The solvent is separated, washed with water then dried over sodium sulfate. The volatiles are removed by distillation to a residue which is dissolved in isopropyl alcohol and the volatiles again removed by distillation to provide a residue. The residue is dissolved in isopropyl alcohol and heated to about 40 to 82° C., preferably about 60° C., filtered, cooled to about 0° C. over about an hour, continued cooling for about an additional two hours and the product collected by filtration and dried further at about 45° C. to give 5,7-dihalo-6-(2,4,6-trifluorophenyl)-[1,2,4]triazolo[1,5-a]-pyrimidine 3 in a purity of >95% as shown by high pressure liquid chromatography (HPLC). Preferably, when phosphorous oxychloride is the halogenating agent, 5,7-dichloro-6-(2,4,6-trifluorophenyl)-[1,2,4]triazolo[1,5-a]-pyrimidine is formed.

In the third step of the process, to a solution of 5,7-dihalo-6-(2,4,6-trifluorophenyl)-[1,2,4]triazolo[1,5-a]-pyrimidine 3 in an aprotic solvent, preferably anhydrous N,N-dimethylformamide (DMF), wherein the ratio of 5,7-dihalo-6-(2,4,6-trifluorophenyl)-[1,2,4]triazolo[1,5-a]-pyrimidine to DMF is about 3-10 mL DMF/g, preferably 4-5 mL/g, is added an amine $R^1R^2CHNH_2$ 4 where $R^1$ and $R^2$ are hereinbefore defined, wherein the mole ratio of 5,7-dihalo-6-(2,4,6-trifluorophenyl)-[1,2,4]triazolo[1,5-a]-pyrimidine 3 to $R_1R^2CHNH_2$ 4 is in the range of about 1:2-1:3, preferably 1:2.5, with stirring at about 20-30° C. for about 24 to 48 h, preferably about 24 hours. The reaction mixture is poured into cold water of about 10-20° C. wherein the volume ratio of DMF to water is about 1:1 to 1:5, preferably about 1:3. Following about 30 minutes of additional stirring the product is collected by filtration washed with water and dissolved in isopropyl alcohol, cooled to about 0° C. over about an hour, stirred for about an additional hour, collected by filtration and dried to give amine 5. Preferably, 5,7-dichloro-6-(2,4,6-trifluorophenyl)-[1,2,4]triazolo[1,5-a]-pyrimidine in anhydrous N,N-dimethylformamide (DMF) is treated with preferred amine (S)-2,2,2-trifluoro-1-methyl-ethylamine at about 20-30° C. for about 24 h and the reaction mixture is added slowly to cold water forming a precipitated solid product. The solid product is filtered, washed with water, and dried to give a crude product. The crude product is crystallized from a mixture of isopropyl alcohol (IPA) and water to give the product in 82% yield and having a 98% HPLC purity and an enantiomeric excess of >99%.

In the fourth step of the process, to a suspension of alkali metal hydride preferably sodium hydride (60% in mineral oil) in anhydrous tetrahydrofuran is added amino alcohol HO—(CH$_2$)$_n$—NR$^3$R$^4$ 6 dropwise over about 10 to about 40° C. preferably at ambient temperature for about 30 minutes wherein the ratio of tetrahydrofuran to aminoalcohol is about 6.5 mL THF/g aminoalcohol. A solution of amine 5 in tetrahydrofuran is added over about 10 to about 30 minutes, wherein the ratio of THF to amine is about 1 mL THF/g. The mixture is heated to about 55-60° C. for about 12 to about 20 h, preferably about 16 h then cooled to about 0-6° C. To the reaction mixture is added water at about 5 to about 15° C., preferably at about 10° C. water in a ratio of about 10 mL water/1 g of amine. The volatiles are removed by distillation to afford a residue which is extracted with a solvent selected from t-butylmethyl ether (TBME), ethyl acetate and toluene and the aqueous phase separated. Dicarboxylic acid, preferably succinic acid (about 6.6 equivalents) is added to the separated aqueous solution and to the aqueous solution is further added a solvent selected from t-butylmethyl ether (TBME), ethyl acetate and toluene and the mixture cooled to about 0° to about 10° C., preferably about 3° C. The solid precipitate is collected by filtration, washed with cold water then preferably TBME and the solid precipitate is dissolved at about 65° to about 80° in water and is crystallized from water, 10 ml water/g of solid precipitate to afford 6-[(substituted) phenyl]-triazolopyrimidine 7 as the pharmaceutically acceptable dicarboxylic acid salt, preferably the succinic acid salt. When 6-[(substituted)phenyl]-triazolopyrimidine 7 as the pharmaceutically acceptable dicarboxylic acid salt, preferably the succinic acid salt and more preferably as the anhydrous salt is treated with a saturated atmosphere of (80-100%) relative humidity of water the hydrated salt and in particular the dihydrated salt of 6-[(substituted)phenyl]-triazolopyrimidine] is formed.

Scheme 1:

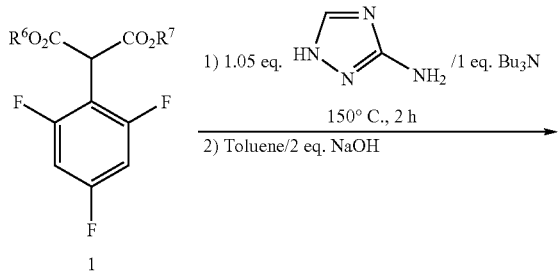

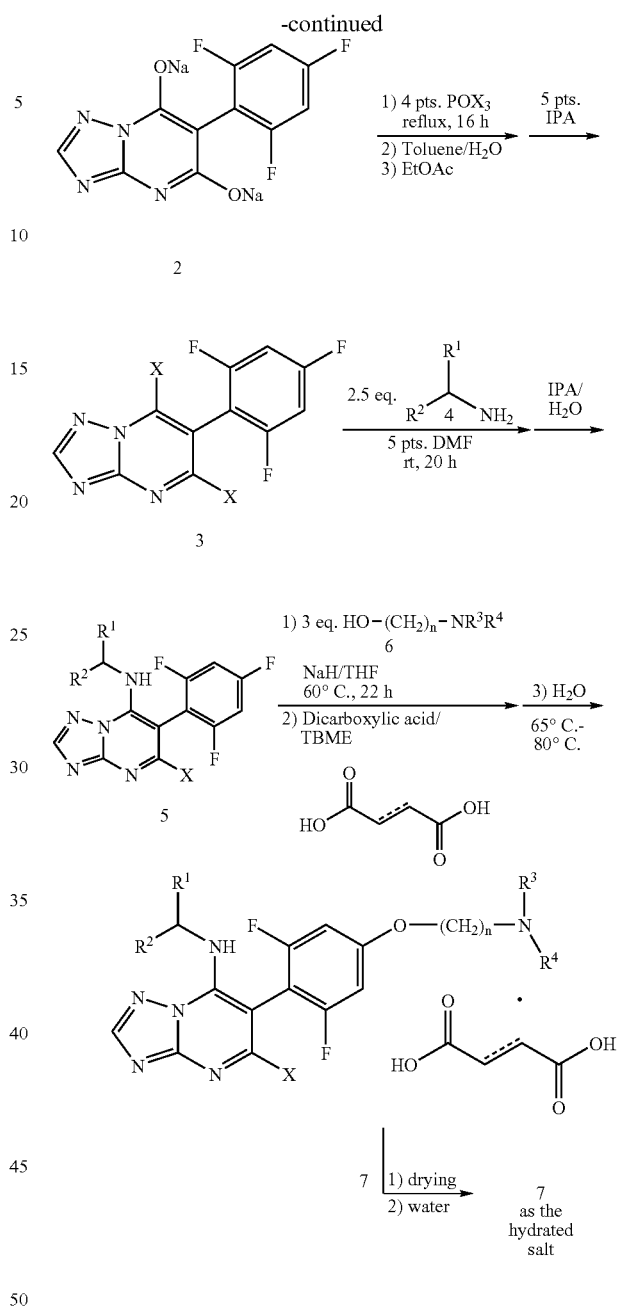

Preferably, coupling of [5-chloro-6-(2,4,6-trifluoro-phenyl)-[1,2,4]triazolo[1,5-a]pyrimidin-7-yl]-((1S)-2,2,2-trifluoro-1-methyl-ethyl)-amine with 3-methylamino-propan-1-ol forms {5-Chloro-6-[2,6-difluoro-4-(3-methylaminopropoxy)-phenyl]-[1,2,4]triazolo[1,5-a]pyrimidin-7-yl}-((1S)-2,2,2-trifluoro-1-methyl-ethyl)-amine in the presence of alkali metal hydride, sodium hydride (NaH), in tetrahydrofuran (THF).

In a typical experiment, to a suspension of sodium hydride (NaH) in THF is added dropwise 3-methylamino-propan-1-ol at ambient temperature and the mixture stirred for about 30 min. A solution of [5-Chloro-6-(2,4,6-trifluoro-phenyl)-[1,2,4]triazolo[1,5-a]pyrimidin-7-yl]-((1S)-2,2,2-trifluoro-1-methyl-ethyl)-amine in THF is slowly added. The mixture is heated to about 60° C. and stirred for about 20 h, then cooled to 0° C. Water is added dropwise while maintaining the temperature at about 10±3° C. The THF is removed by distillation to a residue. The residue is extracted with t-butylmethyl ether (TBME) and to the aqueous phase is added the dicarboxylic acid, in particular succinic acid (6.6 eq.) followed by the addition of TBME. The mixture is cooled to about 3±3° C. and the resulting precipitated solid product is filtered, washed with cold water and TBME. The wet solid at about 65° C. to about 80° C. is dissolved in water and is crystallized to give pure compound in 78% yield and having >99% HPLC purity and an enantiomeric excess of >99% which is dried under vacuum at about 35° C. to about 40° C. to afford the anhydrous salt which is treated with a saturated water atmosphere to afford the hydrated salt.

Optionally, in the salt formation of {5-Chloro-6-[2,6-difluoro-4-(3-methylamino-propoxy)-phenyl]-[1,2,4]triazolo[1,5-a]pyrimidin-7-yl}-((1S)-2,2,2-trifluoro-1-methyl-ethyl)-amine with succinic acid, fumaric acid may optionally replace the succinic acid to form the fumarate salt.

The following examples are presented to illustrate certain embodiments of the present invention, but should not be construed as limiting the scope of this invention.

EXAMPLE 1

Disodium Salt of 6-(2,4,6-trifluorophenyl)-[1,2,4]triazolo[1,5-a]pyrimidine-5,7-diol A mixture of 2-(2,4,6-trifluoro-phenyl)-malonic acid diethyl ester (400 g, 1.38 mol), 3-amino-1,2,4-triazole (122 g, 1.45 mol) and tributylamine (255 g, 1.38 mol) is heated to about 150° C. and stirred for about 2 h. The mixture is cooled to about 130° C. and the heating source is removed. Toluene (1600 mL) is then added over 30 min. The mixture is cooled to room temperature and sodium hydroxide solution (50%, 220 g, 2.76 mol) is added over about 15 min. The mixture is stirred for about 1 h from about 20° C. to about 30° C. The solid is filtered and washed with toluene (2×600 mL) and dried at 80° C./10 mmHg for 40 h to give a white solid (470 g, 105%, >95% HPLC area purity), which is used directly in the next step.

EXAMPLE 2

5,7-dichloro-6-(2,4,6-trifluorophenyl)-[1,2,4]triazolo[1,5-a]-pyrimidine

To phosphorus oxychloride (1900 mL) is added disodium salt of 6-(2,4,6-trifluorophenyl)-[1,2,4]triazolo[1,5-a]pyrimidine-5,7-diol (470 g, 1.38 mol) in portions over about 30 min. The mixture is heated to reflux for about 16 h. The solvent is removed by distillation to a residue and the residue distilled with toluene (2×500 mL). Then, the residue is dissolved into ethyl acetate (1000 mL) and the resulted mixture is poured into water (3000 g) while maintaining the temperature between 5-15° C. The organic phase is separated. The combined organic phase is washed with water (1000 mL) and dried over Na₂SO₄. After most of the solvent is removed by distillation, IPA (2×500 mL) is added and distillation continued to a residue. The residue is dissolved in IPA (2350 mL) and heated to about 60° C. The mixture is filtered at 50-60° C. and the filtrate is cooled to about 0° C. over about 1 h and stirred for about another 2 h. The solid is filtered and dried at 45° C./10 mmHg for 24 h to give a tan solid (243 g, 57%, 96% HPLC area purity).

EXAMPLE 3

[5-Chloro-6-(2,4,6-trifluoro-phenyl)-[1,2,4]triazolo[1,5-a]pyrimidin-7-yl]-((1S)-2,2,2-trifluoro-1-methyl-ethyl)-amine To a solution of 5,7-dichloro-6-(2,4,6-trifluorophenyl)-[1,2,4]triazolo[1,5-a]-pyrimidine (200 g, 0.627 mol) in anhydrous DMF (1000 mL) is added (S)-2,2,2-trifluoro-1-methyl-ethylamine (177 g, 1.57 mol). The solution is stirred from about 20° C. to about 30° C. for 24 h. The reaction mixture is added to cold water (3000 mL) slowly over 30 min. The mixture is stirred for 30 min at 10-20° C. The solid product is filtered and washed with water (2×500 mL). The crude product is dissolved into IPA (1000 mL) at 50° C. Water (2000 mL) is added to precipitate the product over 30 min. The mixture is cooled to 0° C. over 1 h and stirred for 1 h at this temperature. The solid is filtered and dried at 65° C./10 mmHg for 20 h to give a light yellow solid (204 g, 82%, 98% HPLC area purity and 99% ee).

EXAMPLE 4

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine Succinate Salt Dihydrate To a suspension of NaH (40.9 g, 1.02 mol, 60% in oil) in anhydrous THF (750 mL) is added 3-methylamino-propan-1-ol (115 g, 1.21 mol) at about 20-30° C. dropwise over 30 min. The mixture is stirred for 30 min. Then, a solution of [5-chloro-6-(2,4,6-trifluoro-phenyl)-[1,2,4]triazolo[1,5-a]pyrimidin-7-yl]-((1S)-2,2,2-trifluoro-1-methyl-ethyl)-amine (150 g, 0.379 mol) in THF (150 mL) is added slowly over 15 min. The mixture is heated to 60° C. and stirred for 16 h, then cooled to 0-6° C. Cold water (1500 mL) is added dropwise while maintain the temperature between 10±3° C. THF is removed by distillation. The reaction mixture is extracted with t-butylmethyl ether (TBME, 2×1000 mL) and to the separated aqueous phase is added in portions succinic acid (296 g, 2.51 mol) is added in portions and followed by addition of TBME (1000 mL). The mixture is cooled to 3±3° C. and stirred for 1 h. The crude solid product is filtered, washed with cold water (150 mL) and TBME (2×400 mL). The wet solid is dissolved into water (2000 mL) at about 75° C. The solution is filtered at 60-70° C. and cooled to 0° C. over 1 h and stirred for 1 h at this temperature. The solid is filtered and dried at 35° C./10 mmHg for 20 h to give a white solid in anhydrous form (175 g, 80%, >99% HPLC area purity and 99% ee). A small portion of the anhydrous compound is placed in a drying dish of 80%-100% relative humidity at about 20° C. to about 30° C. for 24 h. It absorbed 5.8% wt of water and stopped. This dihydrate is stable at about 20° C. to about 30° C. and at 5%-100% relative humidity. ¹H NMR (CDCl₃): δ 10.2 (bs, 1H), 8.26 (s, 1H), 6.80 (d, 2H, J=10.5 Hz), 5.79 (m, 1H), 4.13 (t, 2H, J=6.3 Hz), 3.03 (t, 2H, J=7.2 Hz), 2.57 (s, 3H), 2.35 (s, 4H), 2.07 (m, 2H), 1.27 (d, J=6.0, 3H).

What is claimed is:

1. A process for the preparation of a 6-[(substituted)phenyl]-triazolopyrimidine dicarboxylic acid salt and as a hydrated salt having the structural formula (I)

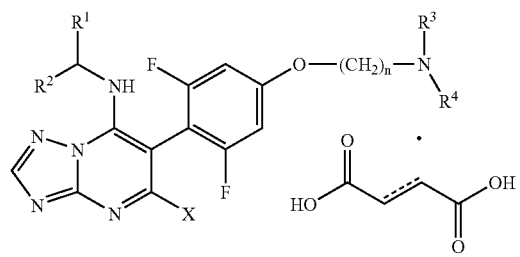

wherein:
$R^1$ is $CF_3$ or $C_2F_5$;
$R^2$ is H or $C_1$-$C_3$ alkyl;
n is an integer of 2, 3, or 4;
X is Cl or Br;
$R^3$ and $R^4$ are each independently H or $C_1$-$C_3$ alkyl; or
$R^3$ and $R^4$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^5$;
$R^5$ is $C_1$-$C_3$ alkyl; wherein the dotted line is an optional bond, which process comprises:

a. reacting a malonic acid ester of the formula

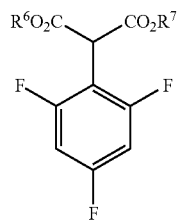

where $R^6$ and $R^7$ are independently $C_1$-$C_3$ alkyl with 3-amino-1,2,4-triazole, in the presence of trialkyl amine base and heating at about 130-170° C., for about 1 to 6 h, cooling to about 130° C., diluting with toluene, cooling to about 20° C. to about 30° C., and adding at least two equivalents of aqueous alkali metal hydroxide (MOH) and isolating the dimetal salt of the formula

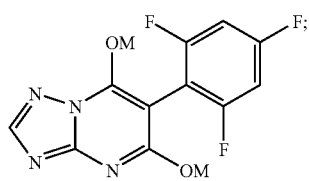

b. halogenating the dimetal salt with a halogenating reagent $POX_3$ where X is Br or Cl to obtain the halogenated product of the formula

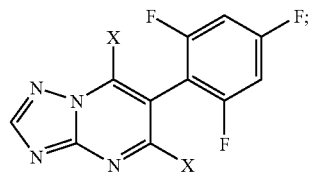

c. reacting the halogenated product with an amine

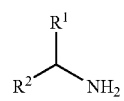

in an aprotic solvent at about 20° C. to about 30° C. to obtain the amine product of the formula

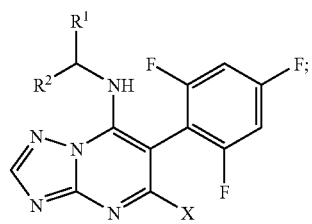

d. reacting an alkali metal hydride with an aminoalcohol HO—$(CH^2)_n$—$NR^3R^4$ for about 30 minutes in tetrahydrofuran at about 10 to 40° C., adding the amine product and heating to about 55-60° C. for about 12 to 20 h, to obtain the 6-[(substituted)phenyl]-triazolopyrimidine product

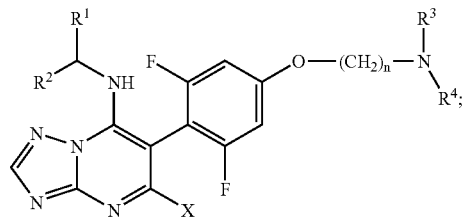

e. reacting the 6-[(substituted)phenyl]-triazolopyrimidine product in water with a dicarboxylic acid of the formula

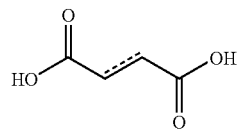

wherein the dashed line is an optional bond and adding a solvent selected from t-butylmethyl ether, ethyl acetate and toluene to obtain the 6-[(substituted)phenyl]-triazolopyrimidine dicarboxylic acid salt as a solid

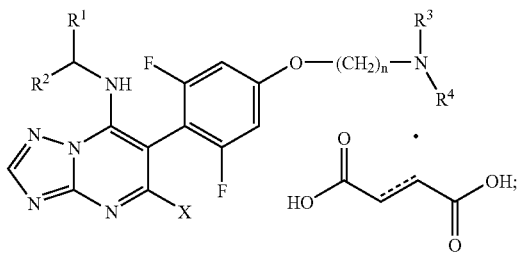

f. crystallizing the 6-[(substituted)phenyl]-triazolopyrimidine dicarboxylic acid salt from water and collecting the 6-[(substituted)phenyl]-triazolopyrimidine dicarboxylic acid salt;

g. forming the anhydrous 6-[(substituted)phenyl]-triazolopyrimidine dicarboxylic acid salt by drying the 6-[(substituted)phenyl]-triazolopyrimidine dicarboxylic acid salt; and h. treating the anhydrous 6-[(substituted)phenyl]-triazolopyrimidine dicarboxylic acid salt with water to obtain a 6-[(substituted)phenyl]-triazolopyrimidine dicarboxylic acid salt of formula (I) as a hydrated salt

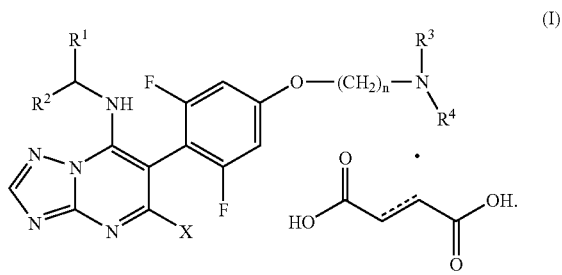

2. The process of claim 1 step a wherein the trialkylamine base is selected from tributylamine and tripropylamine.

3. The process of claim 1 step a wherein the mole ratio of malonic acid ester to 3-amino-1,2,4-triazole is about 1:1.

4. The process of claim 2 wherein the trialkylamine base is tributylamine.

5. The process of claim 1 step a wherein the alkali metal hydroxide is sodium hydroxide.

6. The process of claim 5 wherein the alkali metal hydroxide, sodium hydroxide is about a 50% aqueous solution.

7. The process of claim 1 step b wherein the halogenating reagent is phosphorous oxychloride or phosphorous oxybromide.

8. The process of claim 7 wherein the halogenating reagent is phosphorous oxychloride.

9. The process of claim 1 step e wherein the dicarboxylic acid is fumaric acid.

10. The process of claim 1 step e wherein the dicarboxylic acid is succinic acid.

11. The process of claim 1 step c wherein the aprotic solvent is N,N-dimethylformamide.

12. The process of claim 1 wherein $R^3$ and $R^4$ are each independently H or $C_1$-$C_3$ alkyl.

13. The process of claim 12 wherein $R^3$ is H and $R^4$ is methyl.

14. The process of claim 1 step a wherein the heating is at about 150° C. for about 2 to 3 hours.

15. The process of claim 1 step b wherein the halopenation reaction is heated to reflux for about 8 to 24 hours.

16. The process of claim 15 wherein heating to reflux is for about 16 hours.

17. The process of claim 1 step d wherein the heating is for about 16 hours.

18. The process of claim 1 wherein $R^1$ is $CF_3$ and $R^2$ is methyl.

19. The process of claim 1 step c wherein the amine has the (S) configuration

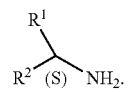

20. The process of claim 1 step e wherein the solvent is t-butylmethyl ether.

21. The process of claim 1 step h wherein treating with water is by a saturated water atmosphere.

22. A process for the preparation of a 6-[(substituted)phenyl]-triazolopyrimidine dicarboxylic acid salt and as a hydrated salt of formula (II)

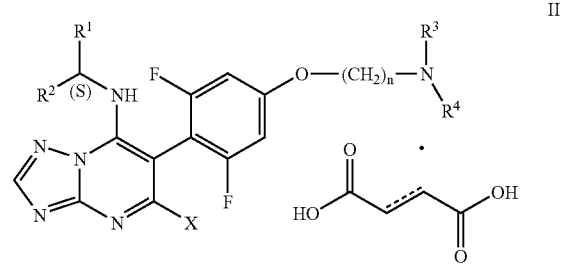

wherein:

$R^1$ is $CF_3$ or $C_2F_5$;

$R^2$ is H or $C_1$-$C_3$ alkyl;

n is an integer of 2, 3, or 4;

X is Cl;

$R^3$ and $R^4$ are each independently H or $C_1$-$C_3$ alkyl;

wherein the dotted line is an optional bond, which process comprises a. reacting a malonic acid ester of the formula

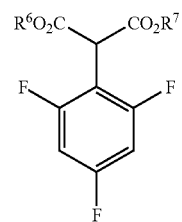

where $R^6$ and $R^7$ are independently $C_1$-$C_3$ alkyl with 3-amino-1,2,4-triazole, in a mole ratio of about 1:1 in the presence of tributylamine and heating at about 150° C. for about 1 to 6 h, cooling to about 130° C., diluting with toluene, cooling to about 20° C. to about 30° C., and adding at least two equivalents of aqueous sodium hydroxide and isolating the disodium salt of the formula

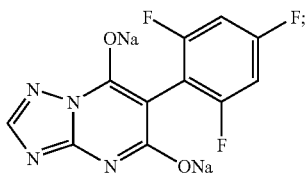

b. halogenating the disodium salt with a halogenating reagent $POX_3$ where X is Cl by heating to reflux for about 16 h to obtain the halogenated product of the formula

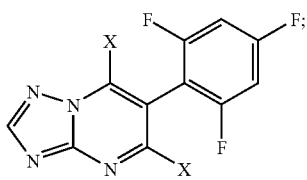

c. reacting the halogenated product with an amine

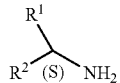

in an aprotic solvent at about 20° C. to about 30° C. for about 24-48 hours to obtain an amine product of the formula

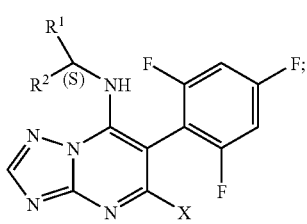

d. reacting an alkali metal hydride with an aminoalcohol HO—$(CH_2)_n$—$NR^3R^4$ for about 30 minutes in tetrahydrofuran at ambient temperature, adding the amine product and heating to about 55-60° C. for about 12-20 hours to obtain the 6-[(substituted)phenyl]-triazolopyrimidine product

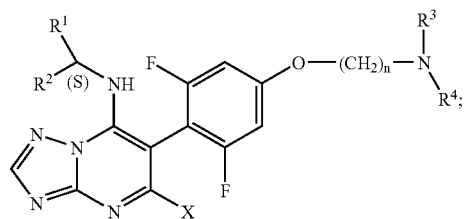

e. reacting the 6-[(substituted)phenyl]-triazolopyrimidine product in water with a dicarboxylic acid of the formula

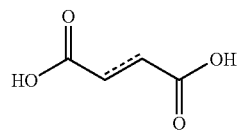

wherein the dashed line is an optional bond and adding t-butylmethyl ether to obtain the 6-[(substituted)phenyl]-triazolopyrimidine dicarboxylic acid salt

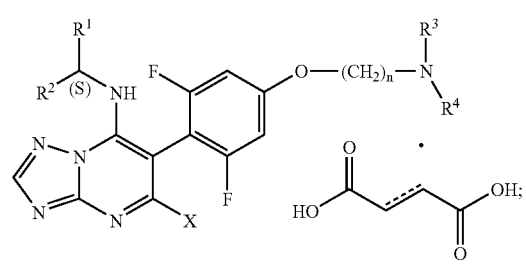

f. crystallizing the 6-[(substituted)phenyl]-triazolopyrimidine dicarboxylic acid salt from water and collecting the 6-[(substituted)phenyl]-triazolopyrimidine dicarboxylic acid salt;

g. forming the anhydrous 6-[(substituted)phenyl]-triazolopyrimidine dicarboxylic acid salt by drying the 6-[(substituted)phenyl]-triazolopyrimidine dicarboxylic acid salt; and h. treating the 6-[(substituted)phenyl]-triazolopyrimidine dicarboxylic acid salt with water in a saturated water atmosphere to obtain a 6-[(substituted)phenyl]-triazolopyrimidine dicarboxylic acid salt as a hydrated salt of formula (II)

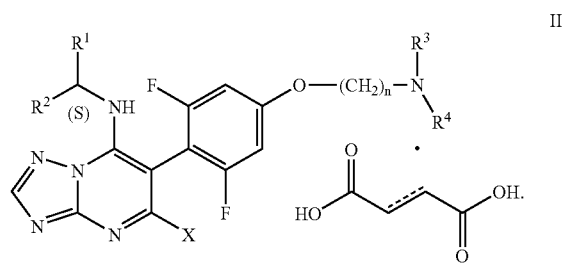

23. The process according to claim 22, step c, wherein the mole ratio of halogenated product to amine is about 1:2 to about 1:3.

24. The process according to claim 1 wherein

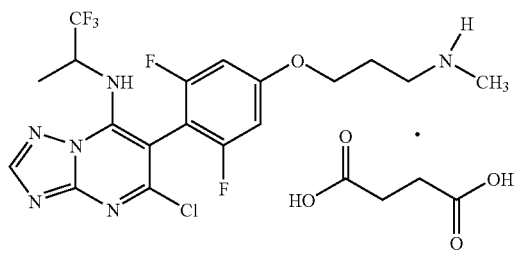

is produced.

25. The process according to claim 1 wherein

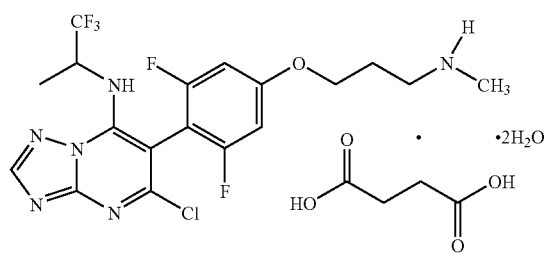

is produced.

26. The process according to claim 22 wherein

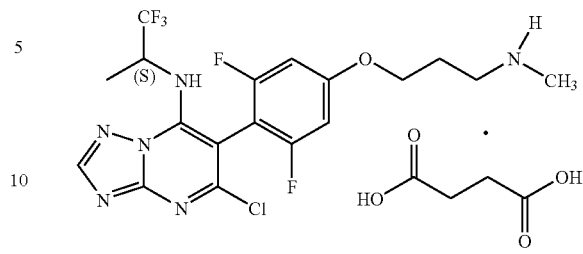

is produced.

27. The process according to claim 22 wherein

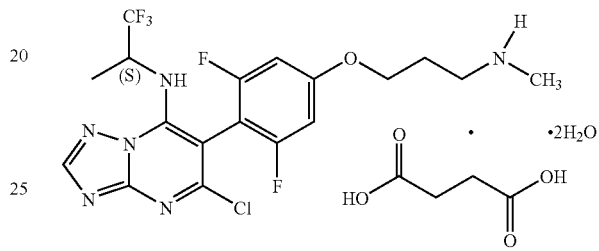

is produced.

28. A process according to claim 1 wherein the mole ratio of halogenated product to amine in step c is about 1:2 to about 1:3.

29. A process according to claim 22 wherein the mole ratio of halogenated product to amine in step c is about 1:2 to about 1:3.

* * * * *